United States Patent [19]

Benita et al.

[11] Patent Number: 5,364,632

[45] Date of Patent: Nov. 15, 1994

[54] MEDICINAL EMULSIONS

[75] Inventors: Simon Benita; Menashe Levy, both of Jerusalem, Israel

[73] Assignee: Yissum Research Development Company of the Hebrew University of Jerusalem, Jerusalem, Israel

[21] Appl. No.: 29,931

[22] Filed: Mar. 9, 1993

Related U.S. Application Data

[63] Continuation-in-part of Ser. No. 795,286, Nov. 19, 1991, abandoned, which is a continuation of Ser. No. 501,266, Mar. 29, 1990, abandoned.

[30] Foreign Application Priority Data

Apr. 5, 1989 [IL] Israel ................................. 89856
Feb. 27, 1990 [IL] Israel ................................. 93558

[51] Int. Cl.$^5$ .......................... A61K 9/127; B01J 13/02
[52] U.S. Cl. ...................................... 424/450; 264/4.1; 514/937; 514/938; 514/939; 514/943
[58] Field of Search ............. 424/450; 264/4.1; 514/937, 938, 941, 943

[56] References Cited

U.S. PATENT DOCUMENTS

| | | | |
|---|---|---|---|
| 4,115,313 | 9/1978 | Lyon et al. | 252/309 |
| 4,703,062 | 10/1987 | Blackburn et al. | 514/552 |
| 4,784,845 | 11/1988 | Desai et al. | 424/80 |
| 4,914,088 | 4/1990 | Glonek et al. | 514/76 |

FOREIGN PATENT DOCUMENTS

| | | |
|---|---|---|
| 0028110A3 | 5/1981 | European Pat. Off. . |
| 0214501 | 3/1987 | European Pat. Off. . |
| 0215313 | 3/1987 | European Pat. Off. . |
| 0253472A1 | 1/1988 | European Pat. Off. . |
| 361928 | 4/1990 | European Pat. Off. . |
| 0391369A2 | 10/1990 | European Pat. Off. . |
| 0399843 | 11/1990 | European Pat. Off. . |
| 0459148A2 | 4/1991 | European Pat. Off. . |
| 0480690A1 | 4/1992 | European Pat. Off. . |
| 8901327 | 3/1989 | WIPO . |
| PCT90/14837 | 12/1990 | WIPO . |

OTHER PUBLICATIONS

Benita et al. Internet. J. Pharmeceut. 30, p. 47, 1986.
Römpp Chemie Lexikon, 9th Edition, p. 1343, item "Fettsäuren," Georg Thieme Verlag, Stuttgart (1990).
Hardberger, R., "Effects of Drug Vehicles on Ocular Contact Time", 93:42–45 (1975).
Patent Abstracts of Japan, vol. 5, No. 200, 18th Dec. 1981, p. 102 C 84; & JP-A-56 122 309.
Enhanced Stability of Physostigmine Salicylate in Submicron O/W Emulsion-Yashwant V. Pathak, et al., 1990, Intl. Journal of Pharmaceutics, 65 (1990) 169–175.

*Primary Examiner*—G. S. Kishore
*Attorney, Agent, or Firm*—Pennie & Edmonds

[57] ABSTRACT

A pharmaceutical composition being an oil in water type emulsion which comprises an effective amount of a lypophilic drug is provided. The composition comprises a synergistic combination consisting of about 3–50% of an oily carrier consisting of MCT oil optionally in combination with vegetable oil, about 0.05%–20% of a phospholipid, about 0.03–10% of a non-ionic surfactant, and about 0.05–5% of an ionic surfactant selected from the group consisting of bile-duct surface active agent, cholic acid and their derivatives.

32 Claims, 5 Drawing Sheets

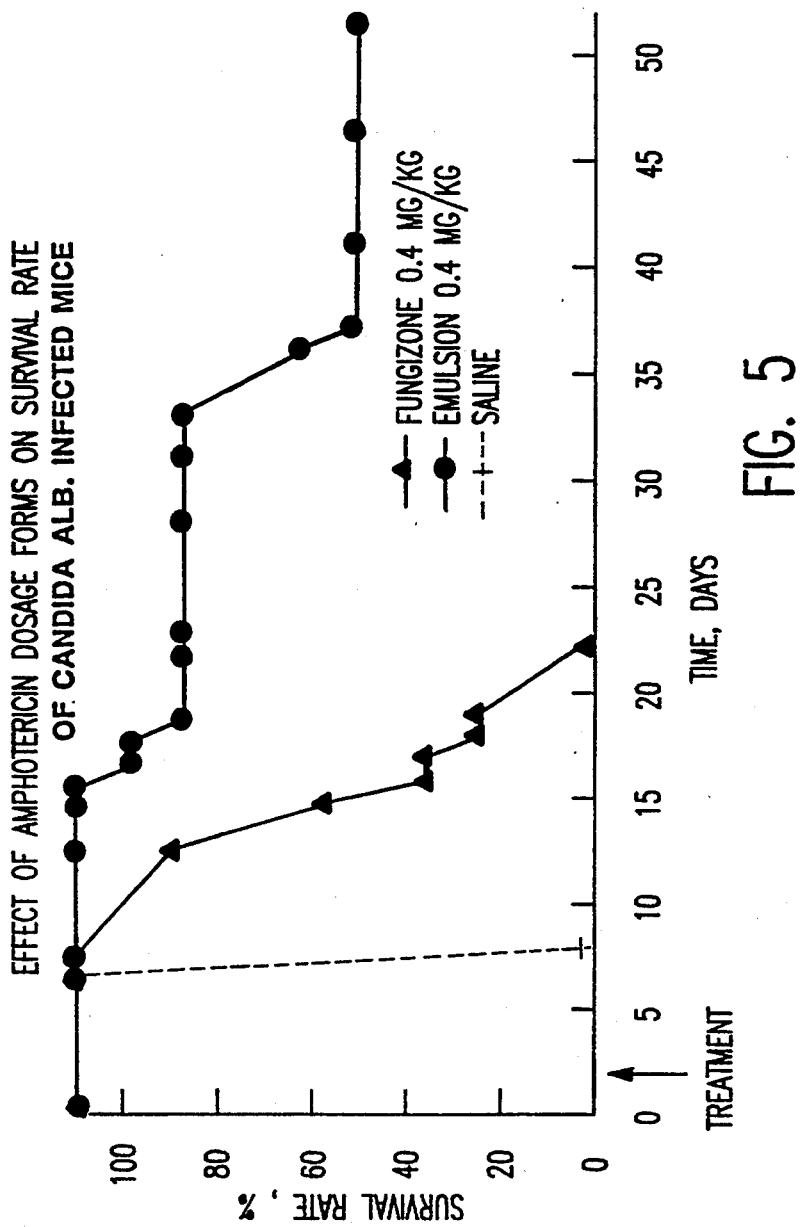

MEDICINAL EMULSIONS

This application is a continuation-in-part of application Ser. No. 795,286 filed Nov. 19, 1991, now abandoned, which is a continuation of application Ser. No. 501,266 filed Mar. 29, 1990, abandoned.

FIELD OF INVENTION

The present invention concerns pharmaceutical compositions of hydrophobic drugs being in the form of an oil-in-water emulsion. The pharmaceutical compositions provided by the present invention show an outstanding long term stability and, in addition, in various forms of administration they also have sustained release characteristics. These pharmaceutical compositions when comprising a heat resistant drug are also remarkably stable to sterilisation by autoclaving.

BACKGROUND OF THE INVENTION AND PRIOR ART

Relevant prior art to the subject of the present invention may be found in the following publications:
1) U.S. Pat. No. 3,172,816.
2) EP-82-214501.
3) EP-A3-215313.
4) Benita, S., Friedman, D. and Weinstock, M. (1986), International Journal of Pharmaceutics, 30: 47–55.
5) Singh, M. and Ravin, J. (1986), J. Parenteral Sci. Technol. 40: 34–41.
6) Von Dardel, O., Mebius, C. and Mossberg, T. (1976), Acta Anaesth. Scand. 20:221–224.

The utilization of pharmaceutical compositions in the form of emulsions of drugs having low aqueous solubility is well known in the art. However, as a rule such compositions are of low stability due to fast phase separation between the oil and the water phases, which is further enhanced by the hydrophobic drugs for which the emulsions serve as carriers.

Many hydrophobic drugs are important for various medical treatments, but since they are relatively unstable and insoluble in water their most useful form of administration is by way of an oil-in-water emulsion-type composition, in which the drug is dissolved in the oil phase. This is in effect the only practical way by which such hydrophobic drugs can be administered intravenously.

In accordance with the prior art stability of compositions of this type was unsatisfactory since as stated above, the hydrophobic drugs destabilize such compositions. Another drawback of prior art emulsion type compositions is that they tend to lose their stability when they are sterilized in an autoclave which is the most efficient and least costly way of sterilizing such compositions. During autoclaving the oily droplets of the emulsion coalesce and consequently creaming and/or phase separation occurs. This therefore necessitated hitherto the use of other forms of sterilization such as filtration.

It is the object of the present invention to provide compositions of the oil-in-water type emulsions containing hydrophobic drugs, which are stable over prolonged storage and furthermore where the drug is heat resistant, are capable of being sterilized by autoclaving without a change in their properties or loss of their stability. It is a further object of the present invention to provide such compositions for parenteral, oral, occular and topical administration of said drug.

GENERAL DESCRIPTION OF THE INVENTION

In accordance with the invention it has surprisingly been found that oil-in-water type emulsions of a hydrophobic drug which comprise an oily carrier being a mid chain triglyceride (MCT) oil optionally in combination with vegetable oil, phospholipids, non-ionic surfactants and an ionic surfactant being a bile-duct surface active agent or a cholic acid derivative are surprisingly more stable than prior art lipophilic drug-containing emulsions both in prolonged storage and in autoclaving.

The improved stability of the compositions in accordance with the invention was found to be caused by a syngergism which exists between the various ingredients, i.e. between said oily carrier, phospholipids, non ionic surfactant and said ionic surfactant.

In the following specification and claims all indication of percent (%) are by weight (w/v—weight of ingredient/volume of entire composition). All concentrations given below should be understood as standing each by itself and not accumulative.

The invention provides a pharmaceutical composition being an oil-in-water type emulsion comprising an effective amount of a hydrophobic drug, characterised in that it comprises about 3–50% of an oily carrier consisting of MCT oil optionally in combination with a vegetable oil, about 0.05–20% of a phospholipid, about 0.03–10% of a non-ionic surfactant, and about 0.05–5% of an ionic surfactant selected from the group consisting of ionic bile-duct surface active agent, cholic acid, their surface active derivatives and their salts.

An oil-in-water type emulsion generally comprises tiny oily droplets comprising the oily carrier (to be referred to hereinafter as the "oily phase") which are suspended in an aqueous solution (to be referred to hereinafter as "the aqueous phase"). The oily droplets are surrounded by a stabilising interfacial film (robe referred to hereinafter for the sake of convenience as the "intermediate phase") formed by the phospholipids, the non-ionic surfactant and the said ionic surfactants.

MCT oil has many advantages over vegetable oil, amongst which are the following: lower susceptibility to oxidation; having a specific density of 0.94–0.95 which is higher than that of vegetable oil and which is close to that of water thus facilitating the obtaining of a stable emulsion; being less hydrophobic than vegetable oil and therefore enables achieving higher concentrations of the drug dissolved therein; having a lower viscosity which again enables obtaining a higher concentration of the oily phase in the composition without substantially increasing its viscosity. Although MCT oil can be considered as a component of vegetable oil, it is separately identified herein because of its particular utility as a preferred oil for use in the present emulsions.

On the other hand, vegetable oil has the advantage over MCT oil in its lower price. Thus, although the use of MCT oil by itself as the oily carrier is generally preferred in accordance with the invention, it may at times be practical to substitute some of it with vegetable oil. Any conventional vegetable oil known to one skilled in the art can be used for this purpose.

Compositions in accordance with the present invention are suitable for topical, parenteral, occular and oral administration of hydrophobic drugs. Preferably the compositions are supplied in unit dosage form. Where a composition of the present invention is to be used for parenteral administration, it must be sterile, which sterilization is preferably performed by autoclaving. The ingredients in compositions to be used for parenteral administration will have to be of injection grade and medically approved for such administration.

An injectable composition should not be too viscous. As a rule, the viscosity of an emulsion increases, with an increase of the relative proportion of the non aqueous phase namely the oily and the intermediate phases, which comprise the oily carrier, phospholipids, non-ionic surfactant, said ionic surfactant and the hydrophobic drug. It is accordingly preferred, in accordance with the present invention, that the relative proportion of the non aqueous phase in injectable composition, should not exceed about 30%. It is even more preferred, in accordance with the present invention, that the relative proportion of the non aqueous phase in injectable compositions be below about 25%.

On the other hand, topical compositions should preferably be viscous and to this end the relative proportion of the non-aqueous phase should preferably be above about 30%.

Thus, the invention relates to an oil-in-water emulsion having a droplet size of between about 0.05 to 0.5 μm for use as a carrier in a pharmaceutical composition. The emulsion consists essentially of about 3–50% (w/v) of a first component of a medium chain triglyceride (MCT) oil or a mixture of the first component with a second component of a vegetable oil; about 0.5–20% (w/v) of a third component of a phospholipid; about 0.3–10% (w/v) of a non-ionic surfactant; and about 0.5–5% (w/v) of an ionic surfactant of cholic acid, deoxycholic acid or a surface active derivative or salt thereof. The first component is preferably used in an amount of between about 5 and 25% and, when it is a mixture, it is preferred to use MCT oil with equal or lesser amounts of the vegetable oil.

The preferred ranges of ingredients of injectable pharmaceutical compositions according to the invention are: oily carrier—about 10–20%; phospholipid—about 0.5–2%, 0.75%–2% being particularly preferred; non-ionic surfactant—about 0.5–3%; said ionic surfactants—about 0.3–10%, 0.5–2% being particularly preferred; drug—about 0.02–2%. Again, these preferred ranges are to be understood as standing each by itself and are not cumulative.

The preferred pH of the aqueous phase of the composition of the invention is about 5.0–8.5, while 6.0–8.0 being more preferred, especially for parenteral administration.

Examples of MCT oil to be used in the compositions of the present invention are TCM (trade name) being a mixture of triglycerides wherein about 95% (w/v) of the fatty acid chains have either 8 or 10 carbon atoms Societe des Oleagineaux, France), Miglyol 812 (trade name being a mixed triester of glycerine and caprilic and capric acids—Dynamit Nobel, Sweden).

Examples of vegetable oil which may be used in the compositions of the present invention are soybean oil, cotton seed oil, olive oil, and sesame oil.

Examples of phospholipids which may be used in compositions according to the invention are lecithins; EPIKURON 170 (trade name) being a mixture of about 70% (w/v) of phosphatidyl choline, 12% phosphatidyl ethanolamine, and about 16% other phospholipids or OVOTHIN 160 (trade name) being a mixture comprising about 60% (w/v) phosphatidylcholine, 18% (w/v) phosphatidyl ethanolamine and (w/v) other phospholipids—both manufactured by Lucas Meyer, Germany) which are mixtures of mainly phosphatidylcholine and phosphatidylethanolamine from a natural source, such as purified egg yolk phospholipids (for the Ovothin series) and such as soybean oil phospholipids (for the Epikuron series); a purified phospholipid mixture; LIPOID E-80 (trade name being a phospholipid mixture comprising about 80% (w/v) phosphatidylcholine, about (w/v) phosphatidylethanolamine, about 3.6% non-polar lipids, and about 2% sphingomyeline—manufactured by Lipoid KG. Ludwigshafen, FRG).

Any nonionic surfactant can be used in this invention. Preferably, the non-ionic surfactant is an alkylene oxide condensate of an organic compound which contains one or more hydroxyl groups. For example, ethoxylated and/or propoxylated alcohol or ester compounds or mixtures thereof are commonly available and are well known to those skilled in the art. Suitable surfactants include, but are not limited to, TYLOXAPOL; POLOXAMER 4070; POLOXAMER 188; POLYOXYL 40 Stearate; POLYSORBATE 80, and POLYSORBATE 20, as well as various compounds sold under the trade name TWEEN (ICI America, Inc., Wilmington, Del., U.S.A.), and PLURONIC F-68 (trade name of BASF, Ludwigshafen, Germany for a copolymer of polyoxyethylene and polyoxypropylene). At this time, PLURONIC F-68 and the POLOXAMER 188 are preferred.

Examples of said ionic surfactant to be used in compositions according to the invention are cholic acid and deoxycholic and surface active derivatives and salts thereof, which may be obtained commercially (e.g. Sigma, St. Louis, Mo., U.S.A.). Any of the conventional salts or surface active derivatives can be used, provided, of course, that they are pharmaceutically acceptable. One skilled in the art can select a particular salt or derivative by conducting routine tests, if necessary. In particular, the alkali metal salts and the taurocholate derivatives are typical of such compounds. Preferred are cholic acid and dexoycholic acid and their sodium salts, deoxycholic acid and its sodium salt being particularly preferred.

The ionic surfactants used in accordance with the invention are anions of relatively weak acids and may thus associate with protons to become electrically neutral when the pH is reduced. Since these substances are surface active in their anionic state, the pH during preparations should be such in which the acid is dissociated into the anions and protons, i.e. the pH should have a higher value than the pKa (pKa—the pH in which half of the acid is dissociated). It was found however that after the composition had already been prepared, there was no reduction in stability even upon lowering of the pH.

The pharmaceutical compositions of the present invention preferably also comprise a preservative such as methyl-, ethyl-, propyl- and butylparaben which are medically accepted for parenteral administration. However, very often in accordance with the invention preservatives will not be required since the compositions may be sterilized by autoclaving without essentially reducing their stability. If desired, the pharmaceutical compositions of the present invention may also comprise an osmotic pressure regulator such as mannitol or glycerin, glycerin being preferred for parenteral administration and mannitol for oral administration. The compositions of the present invention may also comprise an antioxidant such as α-tocopherol.

The compositions of the present invention are suitable for the administration of hydrophobic drugs, i.e. drugs having a low water solubility. Examples of such drugs are: Hydrophobic or lipophilic antibiotic drugs such as amphotericin B; hydrophobic and lipophilic narcotic drugs such as alkaloid bases, e.g. morphine-base; hydrophobic benzodiazepines such as diazepam, fluphenazine deconoate and lorazepam; non-steroidal anti-inflamatory lipophilic drugs such as piroxicamand indomethacin; lipophilic steroids such as protesterone and testosterone propionate; lipophilic azoles such as miconazole and clotrimazole; lipophilic polypeptides such as cyclosporine; lipophilic sterols such as deoxycortone and calciferol; lipophilic cephalosporines; dimercaptol.

Where the drug in such compositions is amphotericin B, its concentration is preferably about 0.015–0.15%, about 0.075% being particularily preferred. Where the drug in said composition is morphine-base, its concentration is preferably about 0.2–2%. Where the drug in said composition is either diazepam or indomethacin, its concentration is preferably about 0.1–1%, about 0.4–0.5% being especially preferred. Where the drug in said composition is ciclosporine, its concentration is preferably about 2–5%. Where the drug in said composition is miconazole, its concentration is preferably about 1–3%.

Generally, the oily droplets in the oil-in-water emulsion for medical use should preferably be small, i.e. below about 1 $\mu$m, since the smaller the droplets, the more stable in storage is the emulsion. The droplet size is advantageously in the size range of about 0.05 to 0.5 $\mu$m and preferably about 0.1 to 0.3 $\mu$m. The droplet size is furthermore of particular importance if the emulsion is to be used for parenteral administration, and especially for intravenous injections, since large droplets will not readily pass through small blood capillaries. The compositions of the invention are particularly suitable for obtaining such small oily droplet.

The compositions of the present invention may be prepared by a number of ways. By one preparation mode, an aqueous solution and an oily solution are separately prepared, the aqueous solution comprising the non-ionic surfactant, the said ionic surfactant and the phospholipids and optionally also an osmotic pressure regulator and a preservative, and the oily solution comprising the said oily carrier, the hydrophobic drug and optionally also an antioxidant. By a slight modification of this mode, the aqueous solution is prepared from two a priori prepared solutions, a first, alcoholic, solution containing the said ionic surfactants and the phospholipid and a second solution containing in water the non-ionic surfactant and if desired also the other optional ingredients mentioned above. The said aqueous solution is then prepared by mixing the first and the second solution, then removing the alcohol, for example by evaporation, to yield the said aqueous solution. This modified mode is suitable for the preparation of composition of the invention in which the drug is for example diazepam or miconazole and the like.

The aqueous solution and the oily solution are then mixed with one another. However, the so-obtained mixture does not yet consist of sufficiently small droplets, the size of which (obtained after mixing with a magnetic stirrer) is about 10 $\mu$m. The droplet size of the inventive composition may then be decreased by the use of emulsification equipment such as Ultra Turrax (Jankl and Kunkel, Staufen, FRG), which yields droplets having an average diameter of about 1.1 $\mu$m, or of a high shear mixer, e.g. Polytron (Kinematica, Lucerne, Switzerland) which yields droplets having an average diameter of about 0.65 $\mu$m.

Especially small droplets are obtained in the inventive compositions when utilizing a two-stage pressure homogenizer in which the crude dispersion is forced under high pressure through the angular space between a spring loaded valve and the valve seat, the second stage being in tandem with the first so that the emulsion is subjected to two very rapid dispersion processes. An example of such an apparatus is the Gaulin Homogenizer (APV Gaulin, Hilversum, The Netherlands). Use of such an apparatus in accordance with the invention yields compositions in which the droplets have an average diameter of about 0.27 $\mu$m with a relatively small deviation.

Even smaller droplets may be obtained in accordance with the invention when the emulsification process combines the use of both a Polytron-type high shear mixer followed by homogenization. The droplet size which is obtained in such a combination is about 0.1–0.15 $\mu$m. These relatively small size droplets are preferred when the emulsion is to be used for intravenous administration or when the formulation is to be sterilized by filtration. While the droplet size has an effect on the composition's stability and is a result of beth the ingredients used for the preparations of the composition, i.e. MCT oil and optionally vegetable oil, phospholipid, non-ionic surfactant and said ionic surfactant as well as the method of preparation as described above, the use of droplet sizes within the range of 0.05 to 0.5 $\mu$m, and preferably 0.1 to 0.3 $\mu$m, provides stable emulsions.

The present invention provides also a novel mode (to be referred to hereinafter as the "inventive mode") for the preparation of the above compositions. The inventive mode is particularly suitable for the preparation of compositions in accordance with the invention in which the drug is both hydrophobic and has a poor oil solubility, i.e. drugs which are present in the compositions, predominantly in the intermediate phase. However, it should be noted that the inventive mode, as will be explained below, is principally suitable also for the preparation of compositions of the invention in which the hydrophobic drug is lipophilic, namely oil soluble and thus present in the compositions predominantly in the oily phase.

In accordance with the inventive mode the compositions are prepared by mixing together a liposome mixture and an oily mixture, each one prepared separately beforehand. The liposome mixture comprises all the ingredients which in the final composition do not form part of the oily phase, namely the phospholipids, the non-ionic surfactant, the said ionic surfactant, and, if desired, also the optional osmotic pressure regulator and the preservative. Where the drug has a poor oil solubility, such as Amphotericin B, it is also included in the liposome mixture. The preparation of the liposome mixture from these ingredients may be carried out by means known per se.

The oily mixture comprises the said oily carrier and, if desired, also the optional anti-oxidant. Where the drug is lipophilic, it is also included in the oily mixture.

After the liposome mixture is mixed together with the oily mixture, an emulsion is formed having relatively large droplets, e.g. about 10 $\mu$m, which is further processed in a similar manner as described above in connection with the first preparation mode, until an emulsion having fine homogenous droplets is obtained.

Compositions of the present invention which contain heat resistant drugs remarkably withstand sterilization in an autoclave. Such sterilization is easier to perform and more practical on industrial scales, than sterilization by filtration as described in EP-A2-214561 and EP-A3-245313. However, where the drugs are heat sensitive, such as Amphotericin B, standard aseptic conditions should be employed.

DESCRIPTION OF SOME SPECIFIC EMBODIMENTS

In the following Examples, the preparation of some specific compositions according to the present invention is described, it being understood that these Examples are for illustrative purposes only and that the invention is not limited thereto.

DESCRIPTION OF THE DRAWINGS

In the following description, reference will at times be made to the annexed drawings in which:

FIG. 5 shows the survivability with time of *Candida albicans* infected mice after injection of Fungizone (trade name), an amphotericin B emulsion in accordance with the invention and of saline.

EXPERIMENTAL METHODS

Figure 1:
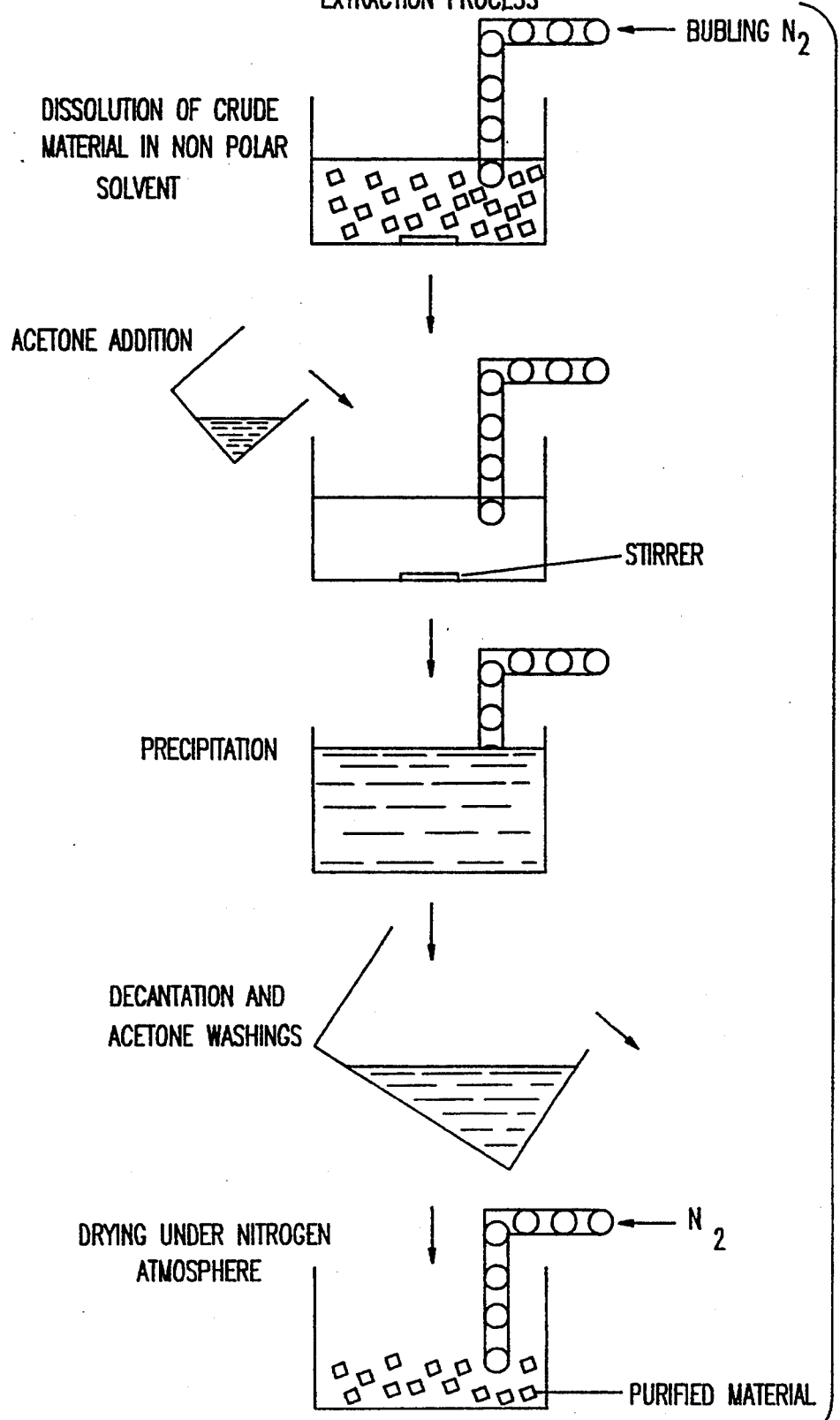
FIG. 1 is a schematic representation of the process for extracting pure phospholipids from crude egg yolk phospholipids.

Measurement of emulsion properties in tests reported in some of the following Examples was performed as follows:

A. Analysis of Particle Size

The droplet size distribution of the Amphotericin B emulsions was determined by two complementary methods, namely by the photon correlation spectroscopy (PCS) using a computerized laser light scattering apparatus, considered the most appropriate for studying droplet size below 1 μm (Malvern system, Malvern, England), and the computerized laser inspection system which can measure droplet sizes above 0.6 μm (Galai Cis-1, Migdal Haemek, Israel). In the Malvern system, each emulsion sample was diluted to the appropriate concentration with a filtered isotonic solution (2.25% glycerin in water) before measurement at 25° C. Duplicate samples were taken and each sample was analysed 10 times. In the Galai system, the samples were also diluted with 2.25% glycerin and two counts were made on each sample. The dilution was needed to increase viscosity thereby reducing the velocity movement of the droplets towards the surface.

The advantage of the Galai Cis-1 system over the widely used Coulter Counter system is demonstrated by the fact that there is no need for an electrolyte solution that can affect the stability of the emulsions. Both methods were needed since none of them was able to measure accurately droplet size of the entire range of 100 to 3000 nm. At most cases, the droplet size of the tested emulsions ranged from 100 to 400 nm. However, when emulsions were subjected to accelerated stability tests, higher mean droplet size could have been in theory expected, and therefor it was necessary to measure diameters in the range of 0.6 to 2.0 μm. Thus, the droplet size distribution of emulsions which underwent stress conditions was analyzed using both the Galai Cis-1 and the Malvern systems.

B. Measurements of Zeta Potential

The zeta potential was measured using the moving boundary electrophoresis technique, which has been shown to yield accurate electrophoretic mobility data. Measurement of electrophoretic mobility and conversion of electrophoretic mobility data to zeta potential, were performed similarly as previously described (Benira, et. al., 1984, J.Pharm. Sci, 73: 1751-1755.), the electrolyte consisted of an aqueous solution containing 1% glycerol and 0.75% Pluronic F-68 which helped to stabilize the moving boundary (preventing the free diffusion of the droplets due to osmotic pressure which occurs in normal aqueous media) without altering the electrophoretic mobility.

Each emulsion sample was diluted with 9 parts of water to 1 part of sample, prior to examination. In order to confirm the measurements reliability various commercial Intralipid (trade name manufactured by Kabi-Vitrum) fat emulsions (which are emulsion used for nutrition, and comprise 10-20% soy oil, phospholipids and glycerin) were measured by this technique and were found to be identical, within the limits of experimental error, to corresponding zeta potential values published in the literature. Further confirmation of the reliability of this method came from the repeatability of results.

C. pH Measurement

The pH of the emulsion samples was measured using a pH meter (radiometer pH M63, Copenhagen, Denmark).

EXAMPLE 1

Preparation of an Emulsion Containing Diazepam

A) Oily, alcoholic and aqueous solutions were separately prepared as follows (all amounts below are given in % w/v in relation to the final total emulsion volume):

I. Oily Solution

The oily solution consisted of the following ingredients:

1) 10% TCM (Societe Industrielle de Oleagineaux, St. Laurent, Blangy, France), and 10% purified soybean oil (Bertin, Courbevoie, France), which was refrigerated for about a week to remove waxy substances.

2) 0.05% α-tocopherol (Sigma Chemicals, St. Louis, Mo., U.S.A.).

3) 0.5% diazepam (Teva Pharmaceuticals Inc., Kfar Saba, Israel).

II. Alcoholic Solution

The alcoholic solution consisted of the following ingredients:

1) 0.5% Deoxy cholic acid—D.C.A. (Sigma, St. Louis, Mo., U.S.A.).

2) 1.0% purified fractionated egg yolk phospholipids, prepared from crude egg yolk phospholipids (Sigma Chemicals, St. Louis, Mo., U.S.A), in accordance with a modification of an earlier technique reported by Schuberth and Wrethind (ACta.

Chit. Scand. Suppl. 278: 1–21, 1961), as represented schematically in FIG. 1 of the annexed drawings. The purification generally consisted of four extraction cycles with petroleum ether 80–100 as extraction solvent. These purified phospholipids consisted mainly of phosphatidylcholine and phosphatidylethanolamine, together with small quantities of phosphatidylserine, phosphaidylinozitol and phosphatidic acids (verified by standard TLC procedure).

III. Aqueous Solution

The aqueous solution consisted of the following ingredients:

1) 2% Poloxamer (Pluronic F-68, BASF, Ludwigshafen, FRG)
2) 2.25% glycerin (Merck, Darmstadt, FRG).
3) 0.2% methyl paraben (methyl p-hydroxybenzoic ester; Sigma Chemicals, St. Louis, Mo., U.S.A.) and 0.075% of butyl paraben (butyl p-hydroxybenzoic ester; Sigma).
4) Double distilled water (DDW) added up to 100%.

Ingredient (3) was not always present and was only added when no autoclaving was to be applied.

The alcohol solution was admixed with the aqueous solutions and the alcohol was removed by evaporation. The so obtained solution is the one which is hereinafter referred to as the "aqueous solution".

Emulsion Preparation

Figure 2:
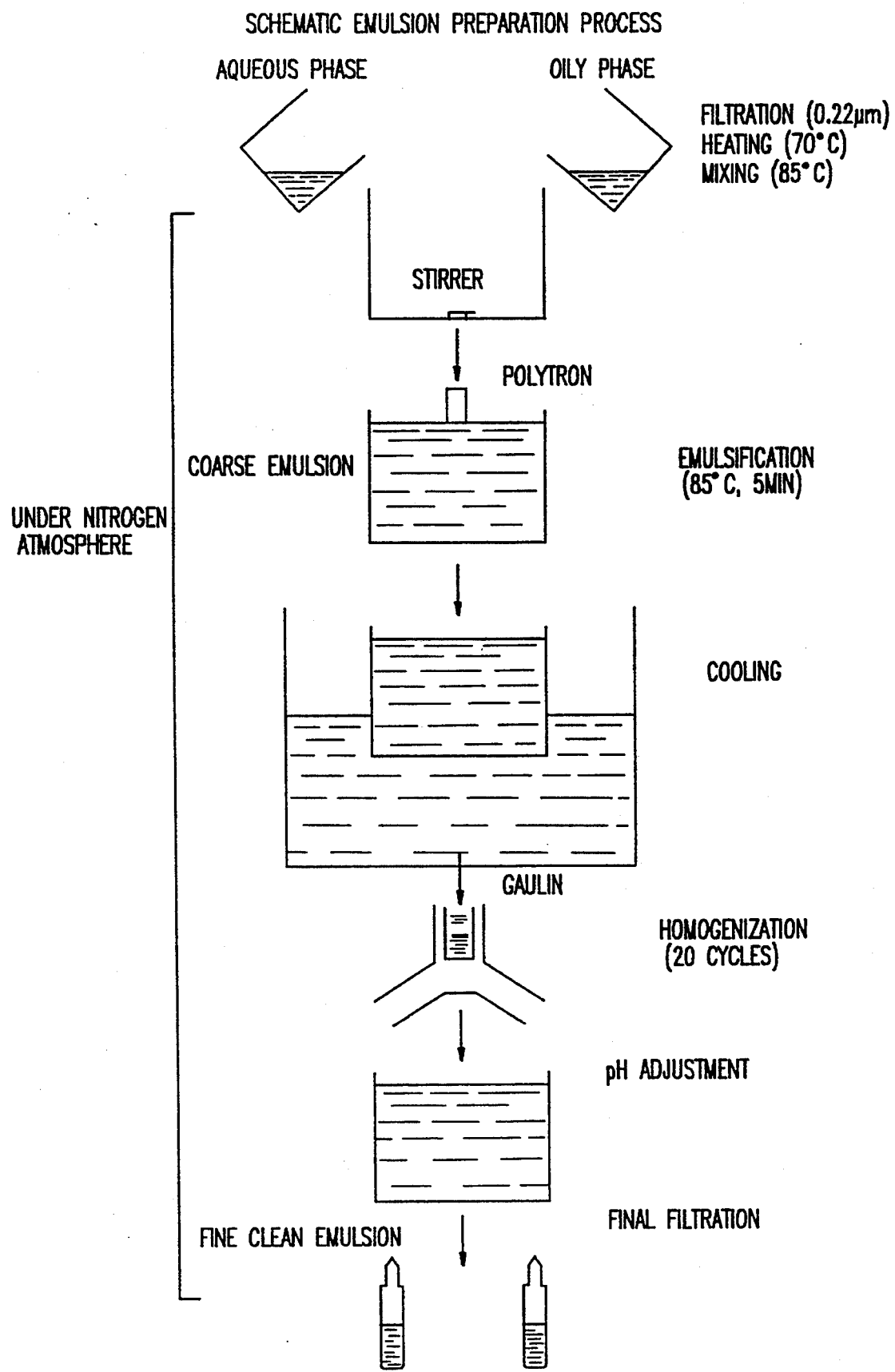
FIG. 2 is a schematic representation of an emulsion preparation process.

The whole process for the preparation of the emulsion was conducted under nitrogen atmosphere and under aseptic conditions. This process is schematically represented in FIG. 2 of the annexed drawings.

Both solutions were appropriately filtered using 0.22 μm millipore membrane filter. After filtration, the aqueous and the oily solutions were heated separately to 70° C. and dispersed by a magnetic stirrer. Further heating was applied while mixing until the temperature reached 85° C. At this temperature, the two solutions were mixed and emulsified during 5 min. using a high shear mixer, [Polytron (trade name) Kinematica, Lucerne, Switzerland]. The resulting coarse emulsion was cooled rapidly below 20° C. A fine monodispersed emulsion (i.e. having a small range of droplet sizes) was then achieved following 20 homogenization cycles, using a two-stage homogenizing valve assembly (Gaulin homogenizer, APV Gaulin, Hilversum, The Netherlands), at a temperature of 40°–70° C. under pressure of about 8500 psi.

Following the homogenization, the pH was adjusted to 8.0 using a 10% sodium hydroxide solution and the emulsion was filtered using a 1 μm filter, to discard the coarse droplets which were generated during the emulsification and homogenization processes and also other debris.

Samples of the so filtered fine clean emulsion were stored in 10 ml brown ampoules and no phase separation was observed over periods of more than fourteen months.

EXAMPLE 2

Preparation of an Emulsion Containing Diazepam

In a similar manner to that described in Example 1, diazepam containing emulsions were prepared, replacing, however, the purified fractionated egg yolk phospholipids (ingredient 3 of the oily solution) with Ovothin 160 (Lucas Meyer, Hamburg, Federal Republic of Germany).

Similarly as in Example 1, no phase separation was seen even after storage of more than twelve months.

EXAMPLE 3

Stability of the Emulsions

The stability of the emulsions of Examples 1 and 2 was determined by measuring various parameters of the emulsion on various time intervals following their preparation. The emulsions were stored at 4° C. Essentially no change in either pH, zeta potential, mean droplet size, droplet size distribution and drug content was observed for more than fourteen months after preparing the emulsions. The stability tests are still under evaluation.

Some batches of the above emulsions were subjected, following their preparation, to a thermal shock by subjecting them to autoclaving—1.1 atm., 121° C., 15 min. Such a thermal shock is considered in the art as an effective accelerated test for assessing emulsion stability. However, surprisingly, even for such emulsions, no loss in stability was observed as determined by measuring the same above parameters similarly as above these emulsions retained their initial properties for more than four months after sterilization was performed.

EXAMPLE 4

Stability of Emulsions Prepared with Either Deoxycholic Acid or Sodium Deoxycholate The emulsion of Example 2 was successively modified to give four different formulations as shown in the following Table I:

TABLE I

| Ingredients | Amount (%) | Formulations | | | |
|---|---|---|---|---|---|
| | | 1 | 2 | 3 | 4 |
| Soybean Oil | | — | 10.0 | — | 10.0 |
| MCT oil | | 20.0 | 10.0 | 20.0 | 10.0 |
| α-tocopherol | 0.02 | + | + | + | + |
| Ovothin 160 | 1.0 | + | + | + | + |
| Diazepam | 0.5 | + | + | + | + |
| Pluronic F-68 | 2.0 | + | + | + | + |
| SDC.* | | — | — | 1.0 | 1.0 |
| DCA.** | | 0.5 | 0.5 | — | — |
| Glycerol | .25 | + | + | + | + |
| Water to | 100 | + | + | + | + |

*SDC. - Sodium deoxycholate
**DCA. - Deoxy cholic acid

The zeta potential and the droplet size of the various formulations is shown in the following Table II:

TABLE II

| Formulation | Droplet size (nm) | | Zeta Potential (mv) |
|---|---|---|---|
| | mean | S.D.* | |
| 1 | 112 | 27.9 | 48 |
| 2 | 117 | 29.8 | 45 |
| 3 | 125 | 31.2 | 35 |
| 4 | 137 | 36.8 | 32 |

*S.D. - standard deviation

It can be seen that the compositions comprising MCT oil as the sole oily carrier had improved properties as compared to those prepared with equal concentrations of both MCT and vegetable oil. Additionally, the results show that emulsions comprising DCA had smaller, more uniform droplets and higher zeta potential than compositions comprising SDC. Hence the preference in utilizing DCA over SDC.

EXAMPLE 5

Synergism between Phospholipids, Non-ionic Surfactant and Deoxycholic Acid in Diazepam Containing Emulsions The emulsion of Example 2 (without α-tocopherol) was successively modified to give emulsions of different formulations as shown in Table III below:

TABLE III

| Ingredient | Concentration in % (w/v) | FI | FII | FIII | FIV | FV | FVI | FVII |
|---|---|---|---|---|---|---|---|---|
| Soybean Oil | 10.0 | + | + | + | + | + | + | + |
| MCT Oil | 10.0 | + | + | + | + | + | + | + |
| Diazepam | 0.5 | + | + | + | + | + | + | + |
| Ovothin 160 | 1.0 | + | + | + | − | + | − | − |
| Poloxamer F-68 | 2.0 | + | + | − | + | − | + | + |
| Deoxycholic acid | 0.5 | + | − | + | + | − | − | + |
| Glycerin | 2.25 | + | + | + | + | + | + | + |
| Distilled water to 100.0 | | + | + | + | + | + | + | + |

All formulations were prepared on the same day with the same reagents and using the same preparative procedure, as described in Example 1. Following preparation the emulsions were sterilized by autoclaving (121° C., 1.1 atm, 15 min.).

The emulsions were first checked visually to determine the degree of creaming and those compositions that remained stable after 1 week were checked further to determine the droplet size and zeta potential.

The following results were obtained:

Formulation FI

This emulsion, which was the one of Example 1, was the most stable one and it remained stable for over fourteen months, and no creaming and phase separation were observed.

Zeta potential of this emulsion was measured to be −45 mv and the mean droplet diameter was measured robe about 117 nm.

Formulation FII

The emulsion was unstable and 3–4 weeks after its preparation phase separation was observed. The phase separation was evident by the appearance of oil drops on the upper surface of the emulsion.

Formulation FIII

Phase separation was observed within one day after preparation of the emulsion.

Formulation FIV

Creaming was observed within a day of preparation of the emulsion. There was a smaller proportion of drops having a larger diameter, which caused creaming, which developed in the course of time to a total phase separation.

Formulation FV

The emulsion was unstable and total phase separation was observed within 2 days.

Formulation FVI

Creaming was observed in the emulsion within a day of its preparation. The degree of creaming increased in the following days resulting finally in a complete phase separation.

Formulation FVII

The emulsion was very unstable and phase separation was already observed in the course of its preparation.

Summary

The emulsion of Formulation FI is the only one containing all the ingredients. The many-fold increase in stability over any of the emulsions of Formulations FII to FVII is attributed to the synergistic action which the oils, phospholipids, non ionic surfacants and deoxycholic acid have on long term stability of the composition.

EXAMPLE 6

The Effect of a Thermal Shock on a Diazepam Containing Emulsions

The emulsions of Example 4 were subjected to a thermal shock by sterilizing in an autoclave (15 min, 121°, 1.180 atm). The mean droplet size (M.D.S.) and the standard deviation (S.D.) were determined before and after autoclaving and the results are given in the following Table IV:

TABLE IV

| Formulation No. | Before autoclaving | | After autoclaving | |
|---|---|---|---|---|
| | M.D.S. | S.D. | M.D.S. | S.D. |
| 1 | 112 | 27.9 | 112 | 29.6 |
| 2 | 117 | 29.8 | 126 | 31.2 |
| 3 | 125 | 31.2 | 150 | 39.4 |
| 4 | 137 | 36.8 | 135 | 37.6 |

The above results show clearly that sterilization had very little effect on droplet size of the emulsions and this remarkable result is in contrast to the instability of hitherto known emulsions of the oil-in water type.

EXAMPLE 7

Stability to Autoclaving of a Micronazole Base Containing Emulsions

In a similar manner to that described in Example 1 an emulsion comprising the following ingredients was prepared (% w/v ):

Miconazole base—1.0; MCT oil—20.0; Ovothin 160—1.0; α-Tocopherol—0.02; Pluronic F-68—2.0; DCA—0.5; Glycerol 2.25; and Water to 100.

The droplet size and standard deviation was measured before and after sterilization in an autoclave as in Example 6 and the results are shown in the following Table V:

TABLE V

| Before autoclaving | | After autoclaving | |
|---|---|---|---|
| M.D.S. | S.D. | M.D.S. | S.D. |
| 135 | 45.9 | 141 | 30.0 |

Here again, the surprising stability of the emulsion to autoclaving is demonstrated.

EXAMPLE 8

Preparation of an Emulsion Containing Amphotericin B

Amphotericin B was dissolved in methanol (0.8 mg/ml) by bath sonication (15 min). Phospholipids E-80 (containing mainly 80% phosphatidylcholine and 8% phosphatidyl ethanolamine according to manufacturer specifications) were dissolved in chloroform. Both solutions were mixed and filtered through a combined filtering system comprising a fiber glass prefilter (GF.92, Schleicher and Schuel, FRG) and 0.45 μm regenerated cellulose membrane filter (RC 5, Schleicher and Schuel, FRG), for removing pyrogens and aggregates. The resulting clear lipid solution was deposited as a thin film on the walls of a round-bottom flask by rotary evaporation under reduced pressure at 40° C. The aqueous phase comprising the poloxamer, sodium deoxycholate and glycerin was filtered through a 0.22 μm Millipore (trade name, manufactured by Millipore, Bedford, Mass., U.S.A.) filter, poured into the flask and the dispersion was sonicated until a homogeneous liposomal mixture was achieved.

MCT oil, filtered through 0.22 μm Millipore filter and containing α-tocopherol was heated to 70° C. and then admixed into the liposomal mixture heated to 45° C. and dispersed therein by a magnetic stirrer. Emulsification was carried out while maintaining the same temperature using a high shear mixer, Polytron (Kinematica, Luzern, Switzerland). The resulting coarse emulsion was cooled rapidly. A fine monodispersed emulsion was achieved using a two stage homogenizer (APV Gaulin, Hilversum, The Netherlands).

Finally, the pH of the emulsion was adjusted to 8.0 with unbuffered 10% sodium hydroxide solution and the 10 final emulsion was filtered through a 0.45 μm Millipore filter to discard coarse droplets and debris generated during the emulsification and homogenization processes.

All the processing operations were carried out under aseptic conditions. The sterility of the emulsions was assessed using the Bactec 46 apparatus (Johnson Laboratories, Towson, Md.). This instrument is used to test inoculated Bactec culture vials for the presence of radioactive Carbon dioxide ($^{14}CO_2$) in the vials. Should a high level of $^{14}CO_2$ be present in vials used for culturing aerobic or anaerobic organisms, it indicates that there were viable microorganisms in the original inoculum. The negative results obtained using this technique showed that the emulsions were sterile.

The relative amounts of the various ingredients in the final emulsions were as follows:
0.075% amphotericin B, 20% MCT oil, 0.5% phospholipid E 80, 2.0% poloxamer, 1.0% sodium dioxycholate, 2.25% glycerine, 0.02% α-Tocopherol and bi-distilled water 200%.

For the purpose of various comparative tests to be reported below, also a plain emulsion, namely one which did not contain any lipophilic drug was prepared under identical experimental conditions.

EXAMPLE 9

Evaluation of the Properties of an Amphotericin B Containing Emulsion

Figure 3A:
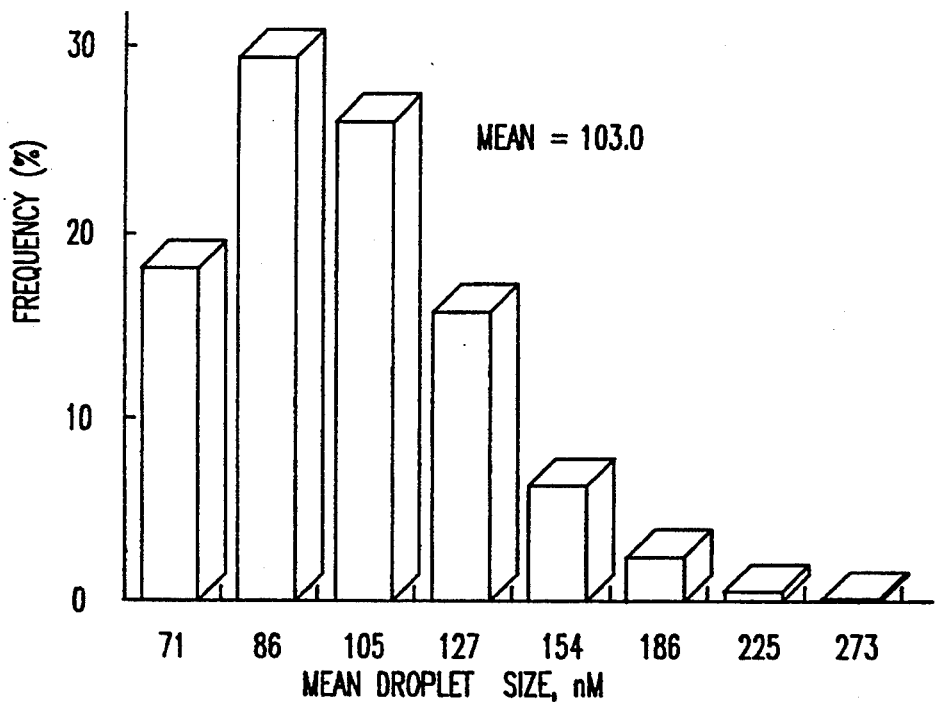
FIG. 3 shows droplet size distribution in a composition not containing any drug (a) and in a composition containing the drug Amphotericin B (b)
Figure 3B:
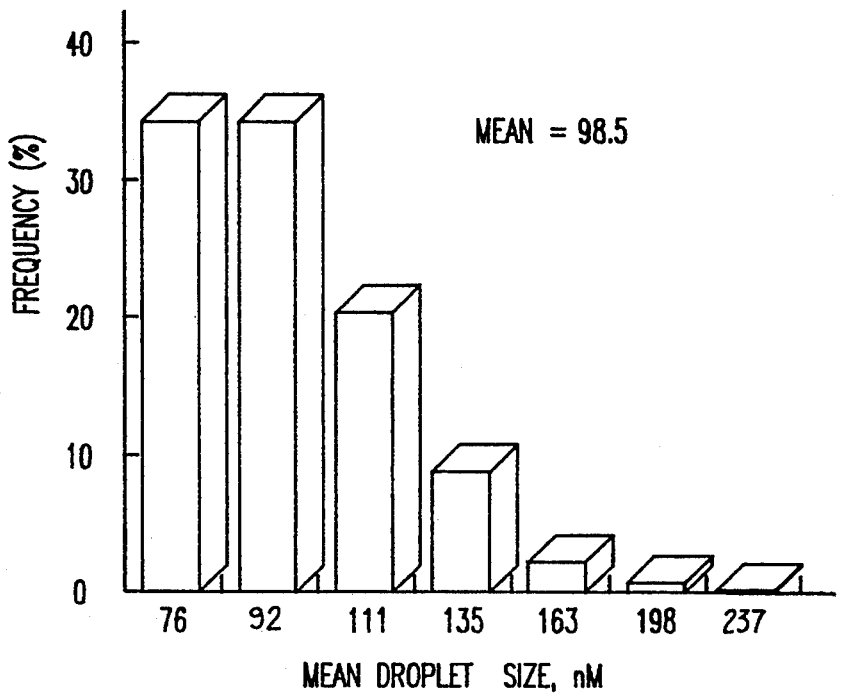

The emulsion of Example 8 was evaluated and found to have a mean droplet size of about 100 nm as shown in FIG. 3. Furthermore, as may be seen in this Figure, no notable difference was found in the droplet size between the amphotericin and the plain emulsion.

This is further shown in the following Table VI:

TABLE VI

| EMULSIONS | MEAN | DROPLET SIZE S.D.(*) | POLY D.(**) | ZETA POTENTIAL (mv) | pH |
|---|---|---|---|---|---|
| PLAIN | 103 | 29.8 | 0.122 | −35.3 | 8.0 |
| WITH AMPHOTERICIN | 97.5 | 23.8 | 0.130 | −32.4 | 8.0 |

(*)S.D. - Standard deviation
(**)Poly D - plydisperity, a factor reflecting the homogenity of the population As maybe seen from Table VI, the droplets' size of the two emulsions were very homogeneous. Furthermore, there was also no notable difference in the zeta potential between the two emulsions.

The amphotericin emulsion of Example 8 was stored for a period of three months at 4° C. After such a storage period, the zeta potential, the pH as well as the particle size distribution of both types of emulsion remained practically unchanged. Furthermore, the amount of amphotericin, determined by HPLC as known per se, did not change for up to three months storage at 4° C., indicating that the stability of amphotericin was not affected by its incorporation in the emulsion.

The amphotericin emulsion was subjected to an accelerated shaking stability test, at a shaking rate of 100 strokes per minute at 25° C. for forty eight hours. No droplets having diameter above 1 μm were detected by the Galai Cis-1 system while a slight and insignificant increase in the droplet size of the emulsion was noted with the Malvern PCS method. These results indicate that the amphotericin emulsion remained stable in spite of the mechanical stress.

Figure 4A:
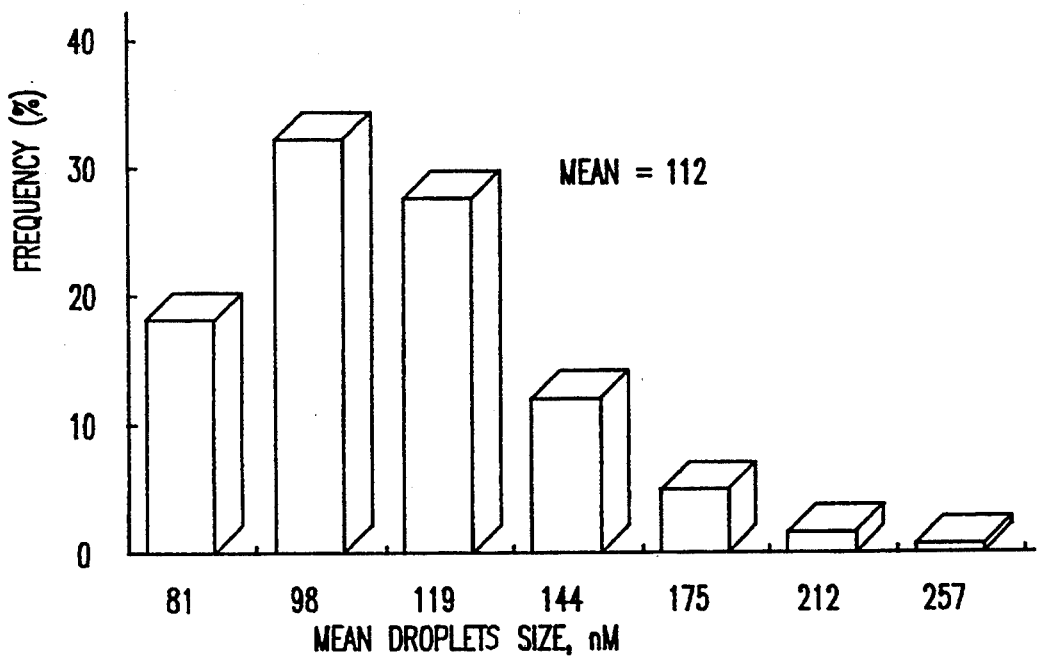
FIG. 4 shows the droplet size distribution after three months storage at 4° C. of compositions containing the drug amphotericin B (a) and compositions containing no lipophilic drug (b).
Figure 4B:
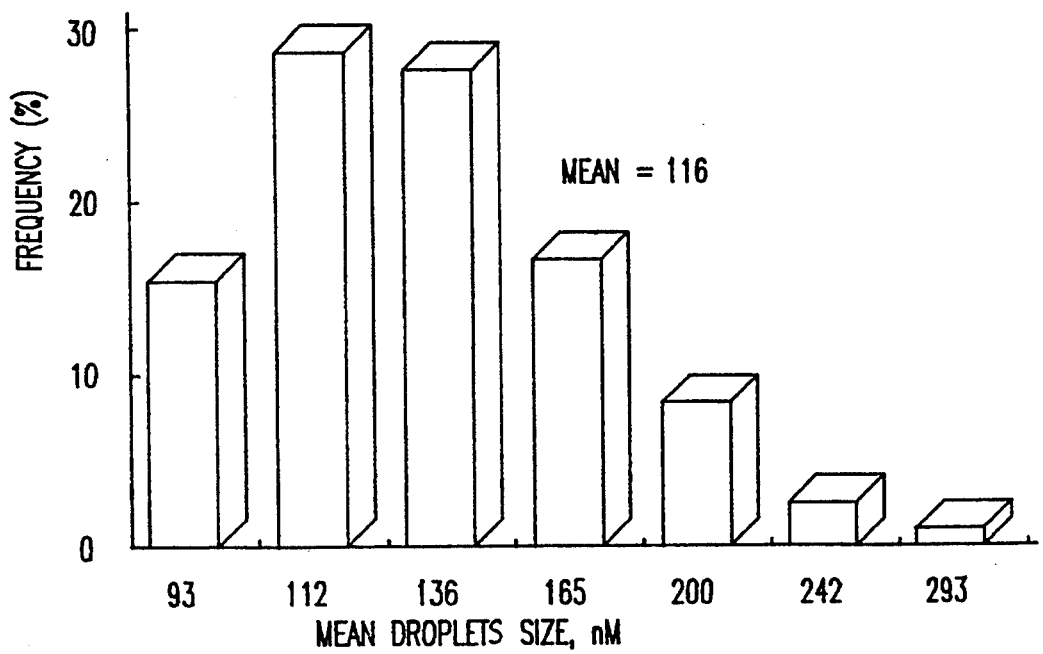

The droplet size distribution of amphotericin emulsion and plain emulsion after three months' storage at 4° C. is shown in FIG. 4. It may be seen that there is no difference between the size distribution of the two emulsions and by comparing these results with those of FIG. 3, it may be seen that there is no substantial difference in the droplet size distribution after storage.

EXAMPLE 10

Animal Studies with Amphotericin Formulations

Thirty balb/c mice ( weighing about 20 g) were injected through the tail vein with $5 \times 10^5$ of *Candida albicans*, strain 562, in 0.1 ml of saline. This dose was shown to cause a total death of the infected mice within five to ten days.

Forty eight hours after the infection was initiated each mouse received a post infection treatment. The mice were divided into three groups of ten mice, each group receiving a different treatment. The treatment consisted of an injection of 0.1 ml into the tail vein of one of the following formulations:

a) Fungizone which is a commercial amphotericin B formulation, (trade name manufactured by E. R. Squib & Sons Ltd) at an amount of 0.4 mg/kg of amphotericin; proper dilution in order to achieve the aforementioned amount was achieved in accordance with manufacturers' specification;

b) An emulsion of Example 8, at an amount of 0.4 mg/kg; dilution of the batch formulation in order to achieve the aforementioned amount was performed with a "plain emulsion" (see Example 8);
c) Saline.

The number of surviving animals in each group was recorded daily, and the survival results are shown in FIG. 5.

It can be seen that all the untreated infected control animals died seven days after *Candida albicans* inoculation. All the infected mice which were treated with Fungizone died from infection 11-19 days after the injection while a much prolonged survival rate was observed in the animals injected with the amphotericin emulsions in accordance with the invention, and 50 days after inoculation, 55% of the mice were alive and appeared in a good condition.

These results demonstrate the improved medical properties of emulsions in accordance with the present invention.

We claim

1. In a pharmaceutical composition consisting essentially of a hydrophobic drug and a carrier, the improvement being in a carrier which is an oil-in-water emulsion of droplet sizes of 0.1 to 0.27 μm consisting essentially of:
   (i) about 3-50% (w/v) of an oily carrier consisting of a medium chain triglyceride (MCT) oil or
   (ii) 0.5-20% (w/v) phospholipids;
   (iii) about 0.3-10% (w/v) of a non-ionic surfactant; and
   (iv) about 0.5-5% (w/v) of a ionic surfactant selected from the group consisting of cholic acid and deoxycholic acid.

2. A pharmaceutical carrier consisting essentially of a hydrophobic drug and a carrier, wherein said carrier is an oil-in-water pharmaceutical composition of a droplet size of about 0.1-0.27 μm
   (i) about 3.50% (w/v) of an oily carrier consisting of a medium chain triglyceride (MCT) oil and up to 50% (w/v) of at least one vegetable oil selected from the group consisting of soybean oil, cotton seed oil, olive oil and sesame oil;
   (ii) 0.5-20% (w/v) phospholipids;
   (iii) about 0.3-10% (w/v) of a non-ionic surfactant; and
   (iv) about 0.5-5% (w/v) of a ionic surfactant selected from the group consisting of cholic acid deoxycholic acid and salts thereof.

3. A carrier according to claim 1 in a form suitable for parenteral administration.

4. A carrier according to claim 1 in a form suitable for topical administration.

5. A carrier according to claim 1 in a form suitable for oral administration.

6. A carrier according to claim 1 in a form suitable for occular administration.

7. A carrier according to claim 2, in which the proportion of the non aqueous phase which comprises said oily carrier, phospholiplids, non-ionic surfactant and said ionic surfactant does not exceed 30% (w/v).

8. A carrier according to claim 7 in which the proportion of said non-aqueous phase does not exceed 25%.

9. A carrier according to claim 1, wherein the relative proportions of the oily carrier is about 10-20% (w/v).

10. A carrier according to claim 1, wherein the relative proportions of the phospholipid is about 0.5-2% (w/v).

11. A carrier according to claim 10, wherein the relative proportion of the phospholipid is about 0.75% (w/v).

12. A carrier according to claim 1, wherein the proportion of the said ionic surfactant is about 4-6.6% (w/v).

13. A carrier according to claim 1, wherein the non ionic surfactant is Poloxamer.

14. A carrier according to claim 1, wherein the said ionic surfactant is selected from the group consisting of cholic acid, deoxycholic acid and their sodium salt.

15. A composition according to claim 1 wherein said hydrophobic drugs are selected from the group consisting of antibiotics or narcotic drugs or non-steroidal anti-inflammatory hydrophobic drugs, hydrophobic steroids, hydrophobic azoles, hydrophobic polypeptides, hydrophobic cephalosporines and dimercaptol.

16. A carrier according to claim 14, wherein said drug is selected from the group consisting of amphotericin B, morphine-base, diazepam, fluphenazine deconate, lorazepam, piroxicam, indomethacin, progesterone, testosterone propionate, miconazole, clotrimazole, cyclosporine, deoxycortone, calciferol, cephalosporine and dimercaptol.

17. A carrier according to claim 16, wherein said hydrophobic drug is amphotericin B.

18. A Composition according to claim 16, wherein said hydrophobic drug is diazepam.

19. A carrier according to claim 16, wherein said hydrophobic drug is morphine, indomethacin, cyclosporine or miconazole.

20. A pharmaceutical composition comprising a drug and a carrier wherein the carrier is an oil-in-water pharmaceutical composition consisting essentially of:
   (i) about 3-50% (w/v) of
      (a) a first component of a medium chain triglyceride (MOT) oil; or
      (b) a mixture of the first component with a second component of a vegetable oil, wherein the amount of the second component of the mixture is present in an equal or lesser amount compared to the first component;
   (ii) about 0.5-20% (w/v) of a third component of a phoepholipid;
   (iii) about 0.3-10% (w/v) of a non-ionic surfactant; and
   (iv) about 0.5-5% (w/v) of an ionic surfactant selected from the group consisting of cholic acid, deoxycholic acid, a taurocholate, or a salt thereof; wherein the pharmaceutical composition has a droplet size of between about 0.05 to about 0.27 μm.

21. The pharmaceutical composition of claim 20 wherein the first component or mixture of first and second components is present in an amount of about 5-25%.

22. The pharmaceutical composition of claim 20 wherein the second component of the mixture is present in an amount of 10% or less.

23. The pharmaceutical composition of claim 20 wherein the first component or mixture of first and second components is present in an amount of about 10-20%.

24. The pharmaceutical composition of claim 20 wherein the cholic acid or deoxycholic acid is in the form of the sodium salt.

25. The pharmaceutical composition of claim 20 wherein the vegetable oil is soybean oil, cottonseed oil, olive oil or sesame oil.

26. The pharmaceutical composition of claim 20 wherein the phospholipids are present in an amount of about 0.75 to 2%.

27. The pharmaceutical composition of claim 20 wherein the phospholipids are selected from the group consisting of lecithin, mixtures of lecithin, and phosphatidylethanolamine, or soybean oil phospholipids.

28. The pharmaceutical composition of claim 20 wherein the non-ionic surfactant is a copolymer of polyoxyethylene and polyoxypropylene.

29. The pharmaceutical composition of claim 20 wherein the non-ionic surfactant is present in an amount of about 0.5 to 2%.

30. The pharmaceutical composition of claim 20 wherein the ionic surfactant is present in an amount of about 0.5 to 2%.

31. The pharmaceutical composition of claim 20 wherein the drug is hydrophobic.

32. The pharmaceutical composition of claim 20 wherein the ionic surfactant is an alkali metal salt.

* * * * *

UNITED STATES PATENT AND TRADEMARK OFFICE
CERTIFICATE OF CORRECTION

PATENT NO. : 5,364,632

DATED : November 15, 1994

INVENTOR(S) : Simon Benita and Menashe Levy

It is certified that error appears in the above-identified patent and that said Letters Patent is hereby corrected as shown below:

In Claim 1, Col. 15 at line 27 the word "or" should be replaced by -- ; --.

In Claim 2, Col. 15 at line 38 the number "3.50% should be replaced by -- 3 - 50% --.

In Claim 6, Col. 15, at line 57 change "occular" to -- ocular --;

In Claim 20, Col. 16, at line 37 change "MOT" to -- MCT --.

In Claim 20, Col. 16, at line 44 change "phoepholipid" to phospholipid.

Signed and Sealed this

Twenty-eight Day of March, 1995

Attest:

BRUCE LEHMAN

*Attesting Officer*        *Commissioner of Patents and Trademarks*